(12) United States Patent
Eugster et al.

(10) Patent No.: US 11,617,495 B2
(45) Date of Patent: Apr. 4, 2023

(54) MEDICAL ENDODEVICE

(71) Applicant: UNIVERSITÄT BASEL, Basel (CH)

(72) Inventors: Manuela Eugster, Emmen (CH); Patrick Weber, Würenlos (CH); Georg Rauter, Eiken (CH)

(73) Assignee: UNIVERSITÄT BASEL, Basel (CH)

( * ) Notice: Subject to any disclaimer, the term of this patent is extended or adjusted under 35 U.S.C. 154(b) by 252 days.

(21) Appl. No.: 16/624,990

(22) PCT Filed: Jun. 25, 2018

(86) PCT No.: PCT/EP2018/066947
§ 371 (c)(1),
(2) Date: Dec. 20, 2019

(87) PCT Pub. No.: WO2019/002202
PCT Pub. Date: Jan. 3, 2019

(65) Prior Publication Data
US 2020/0170707 A1 Jun. 4, 2020

(30) Foreign Application Priority Data
Jun. 26, 2017 (EP) .................................. 17177760

(51) Int. Cl.
*A61B 18/24* (2006.01)
*A61B 34/30* (2016.01)
(Continued)

(52) U.S. Cl.
CPC .......... *A61B 1/00085* (2013.01); *A61B 18/24* (2013.01); *A61B 34/30* (2016.02);
(Continued)

(58) Field of Classification Search
USPC .......................................................... 606/15
See application file for complete search history.

(56) References Cited

U.S. PATENT DOCUMENTS

2005/0080318 A1* 4/2005 Squicciarini ....... A61B 1/00096
600/114
2005/0234296 A1 10/2005 Saadat et al.
(Continued)

FOREIGN PATENT DOCUMENTS

WO 85/02532 A1 6/1985

OTHER PUBLICATIONS

International Search Report dated Aug. 20, 2018 in corresponding International Patent Application No. PCT/EP2018/066947.
(Continued)

*Primary Examiner* — Scott Luan
(74) *Attorney, Agent, or Firm* — Medler Ferro Woodhouse & Mills PLLC

(57) ABSTRACT

A medical endodevice for an intervention inside a human or animal body includes an elongated liaising structure having a distal end arrangeable inside a body of the human or animal being and a proximal end arrangeable outside the body while the distal end is inside the body. The endodevice has an intervention tool arranged to manipulate a target tissue inside the human or animal body. The intervention tool is arranged at the distal end of the liaising structure. The endodevice further includes a positioning unit having a moving formation arranged to dislocate the intervention tool relative to the target tissue, and an anchoring formation arranged to fix the moving formation to a fixing tissue inside the human or animal body such that the target tissue is positioned in a workspace of the intervention tool.

14 Claims, 4 Drawing Sheets

(51) Int. Cl.
  *A61B 1/00* (2006.01)
  *A61B 34/20* (2016.01)
  *A61B 18/00* (2006.01)

(52) U.S. Cl.
  CPC . *A61B 1/00147* (2013.01); *A61B 2018/00196* (2013.01); *A61B 2018/00279* (2013.01); *A61B 2018/00565* (2013.01); *A61B 2018/00577* (2013.01); *A61B 2018/00982* (2013.01); *A61B 2034/2055* (2016.02); *A61B 2034/301* (2016.02)

(56) References Cited

U.S. PATENT DOCUMENTS

| | | | |
|---|---|---|---|
| 2011/0009696 A1* | 1/2011 | Miyoshi | A61B 1/00154 600/114 |
| 2012/0220992 A1* | 8/2012 | Bruno | A61B 34/30 606/13 |

OTHER PUBLICATIONS

Communication pursuant to Art. 94(3) EPC dated Feb. 24, 2023 in EP Appl. No. 18 733 276.2.

* cited by examiner

MEDICAL ENDODEVICE

TECHNICAL FIELD

The present invention relates to a medical endodevice according to the preamble of independent claim 1. Such endodevices comprising an elongated liaising structure having a distal end arrangeable inside a body of a human or animal being and a proximal end arrangeable outside the body while the distal end is inside the body, and an intervention tool arranged to manipulate a target tissue inside the human or animal body, wherein the intervention tool is arranged at the distal end of the liaising structure, can be used for a minimal invasive intervention inside the human or animal body.

BACKGROUND ART

For allowing minimal invasive interventions inside a human or animal body, it is known to use devices which are forwarded through a body lumen to a target location. There, a suitable tool of the device such as a drill, a saw or the like intervenes tissue at the target location. For example, it is known to equip an endoscope with a tool, to forward the endoscope face through a body lumen and to apply the tool at a target location reached via the body lumen.

In recent years, the precision of devices like endoscopes and of the tools used with endoscopes has increased. For instance, in order to precisely controlling the endoscopes, robots are used which allow to provide sophisticated movements. Thereby, even though it was possible to have the robots to autonomously execute interventions typically operators stay involved (robot guided interventions).

With respect to the intervention tools used with endoscopes or similar devices, sophisticated instruments have been developed allowing generating precise and geometrically flexible interventions. For example, laser beams can be used for cutting or drilling hard tissue such as bone tissue or cartilage tissue. Thereby, a laser device generates laser pulses of predefined width and intensity. The pulses are directed to the tip of the endoscope, e.g. via a laser fiber, and from there beam pulses are propagated towards the target tissue. When hitting the target tissue, the laser beam pulses ablate the tissue such that holes, cuts and similar interventions can be applied to the tissue.

Today, problems in such known devices, particularly when being manually operated or controlled, arise from the fact that the precision of locating the face of the endoscope or similar device inside the body lumen typically is lower than the precision of intervention by the tool at the face of the endoscope. This might result in that the exact intervention to the target tissue by the tool is jeopardized by the lower precision of forwarding the endoscope. Therefore, there are systems in consideration which allow for increasing precision in locating the tool inside the body. For example, there are imaging procedures such as computer tomography used allowing to more precisely localizing the face of the endoscope inside the body. However, such procedures typically are cumbersome and comparably slow.

Furthermore, in operation, movements of the part of the endoscope outside the body may affect the tool inside the body during intervention. For example, a person touching or hitting the endoscope outside the body or the robot guiding the endoscope may result in movements of the tool inside the body. This affects the intervention such that its quality and precision may be lowered.

Therefore, there is a need for a system or device allowing a precise minimal invasive intervention inside a human or animal body.

DISCLOSURE OF THE INVENTION

According to the invention this need is settled by a medical endodevice as it is defined by the features of independent claim 1. Preferred embodiments are subject of the dependent claims.

In particular, the invention deals with a medical endodevice for an intervention and particularly a surgical intervention inside a human or animal body. Thereby, the endodevice can be suitable for a so-called minimally invasive intervention or a minimally invasive surgery. Surgery by definition is invasive and many operations require incisions of some size, particularly in open surgery. However, minimally invasive surgery involves surgical techniques that limit the size of incisions needed. Thus, whereas open surgery usually leaves comparably large wounds that are painful and take a long time to heal, minimally invasive surgery lessens wound healing time, associated pain and risk of infection. As other known instruments, the endodevice allows for being entered into a body either via an already existing opening of the body or via a comparably small cut opening towards the interior of the body such as towards a body lumen.

The term "endodevice" in connection with the invention relates to a device which is arranged or embodied to be introduced into a body or body lumen and to be advanced through the body or body lumen to a target location where the intervention is to be executed. Thereby, the term "in the body" or "inside the body" can mean any location in the human or animal body and particularly a quasi embedded location which is not directly accessible from the outside. For example, in the body can mean in between different tissues of the body, such as in between a bone and its surrounding tissue, or inside a body lumen. The term "body lumen" can relate to an inside space of a tubular structure in a human or animal body or to a cavity inside the human or animal body. For example, the body lumen can be a vascular vessel, such as a vein or an artery or a coronary or intracranial vessel or a heart valve, or a tract of a gastrointestinal organ such as stomach or colon, or a region of urinary collecting ducts or of renal tubes, or an interior space of a joint, or a mouth or ear, or a combination thereof. The endodevice can be or comprise a rigid or particularly a flexible endoscope, a catheter, a laparoscope, a colonoscope or a similar arrangement.

The endodevice according to the invention comprises an elongated liaising structure, an intervention tool and a positioning unit. The liaising structure has a distal end arrangeable inside a body of a human or animal being and a proximal end arrangeable outside the body while the distal end is inside the body. The intervention tool is arranged at the distal end of the liaising structure. It is embodied to manipulate a target tissue inside the human or animal body, e.g., accessible via a body lumen.

The term "proximal" as used herein can relate to a direction towards an operator of the endodevice or a machine such as a robot controlling the endodevice. Analogously, the term "distal" can relate to a direction away from the operator or machine.

The term "manipulating the target tissue" as used in connection with the intervention tool can relate to any intervention to the target tissue such as drilling a hole, cutting, grinding, reshaping, a combination thereof or the like. The term "workspace" in connection with the intervention tool relates to a space or environment in which the intervention tool can manipulate the target tissue. Thus, it can be the operating volume which can be reached by the intervention tool.

The positioning unit has a moving formation arranged or configured to dislocate the intervention tool relative to the target tissue, and an anchoring formation arranged or configured to fix the moving formation or positioning unit to a fixing tissue inside the human or animal body such that the target tissue is positioned in a workspace of the intervention tool.

The fixing tissue can particularly be a hard tissue such as the tissue of a comparably rigid structure, e.g., at least one bone, cartilage, tooth, a combination thereof or the like. The target tissue can form part of the rigid structure or it can be a tissue of another distinct rigid or soft structure. Thus, the target tissue can be the same tissue or element as the fixing tissue, or it can be a different tissue or element.

The term "fix" as used in connection with the anchoring formation relates to locating the moving formation in an essentially non-variable position or at an essentially predefined location relative to the fixing tissue. Thereby, the moving formation can be rigidly mounted to the fixing tissue whereas by means of the moving formation the intervention tool can still be moved relative to the target tissue in a precise and well-defined manner in any number of degrees of freedom. In particular, fixing the moving formation to the fixing tissue relates to locating the moving formation in a predefined relation to the fixing tissue. Like this, it can be prevented that the moving formation is moved relative to the fixing tissue other than by the moving formation itself such as, e.g., by the liaising structure or any acting structure of the body such as a muscle or the like. More particularly, when being fixed to the fixing tissue, the moving formation can precisely locate and orientate the intervention member without being affected by external impacts or disturbances and without having to compensate any such impacts or disturbances. Thus, the combination of anchoring and moving formations in the positioning unit according to the invention allows for an efficient and robust implementation of a highly accurate mechanism to direct the intervention member.

The anchoring formation can be embodied in any suitable manner allowing sufficient fixation of the positioning unit to the fixing tissue. For example, it can comprise screw or pin means for being screwed or pinned to the fixing tissue. Like this, a comparable robust fixation can be provided. Or, it can comprise a suction mechanism for sucking the anchoring formation to the fixing tissue. This allows for flexibly fixing and releasing the positioning unit to and from the fixing tissue without affecting the fixing tissue.

The endodevice according to the invention allows for separating the positioning of the intervention tool from its intervention movement. In particular, when advancing the distal end of the endodevice in the body a quasi approximate position relative to the target tissue is sufficient. It is important that the target tissue is in the workspace of the intervention tool. Then, the positioning unit and its moving formation can be fixed to the fixing tissue such that it is robustly connected to the fixing tissue. Now, the moving formation can relocate the intervention tool such that a comparably precise intervention to the target tissue by means of the intervention tool can be achieved. Also, undesired relative motions between the positioning unit and the anatomy of interest can be reduced by construction.

Furthermore, the endodevice allows that even a minimal invasive intervention with a hand held device is possible. No robot or other automatic control is needed that holds and guides the endoscope with sufficient preciseness. Rather, by means of the positioning unit, the endodevice itself can do precise enough positioning. Like this, a precise minimally invasive intervention is possible without requiring complicated and costly control apparatus.

Thus, the endodevice according to the invention allows for separating the positioning movement of its distal end or of its intervention tool from the intervention movement which can then be executed independent from the positioning movement. Like this, a robust and conveniently to handle application can be provided allowing a precise minimal invasive intervention inside the human or animal body. Also, inspection and non-contact examination of the target tissue, such as by ultrasound or infrared light or the like, can be performed by the endodevice.

The intervention tool can be or comprise a conventional mechanical intervention member such as a saw, a drill, a rotary cutter, a burr, a biopsy instrument, a palpation member or the like. Preferably, the endodevice comprises a laser arrangement, wherein the intervention tool is a laser beam propagating structure of the laser arrangement. Such laser devices are becoming increasingly popular since they allow ablating bone or other hard tissue in a very precise and gentle manner without requiring mechanical interaction forces. As such lasers allow for providing a comparably high precision, the endodevice and particularly its positioning unit can be specifically advantageous.

Thereby, the laser beam propagating structure of the laser arrangement preferably comprises an adjustable optics arranged or configured to direct the laser beam in various directions. The optics can particularly comprise at least one mirror. Such an optics allows for precisely directing the laser beam such that a broad variety of intervention geometries can be implemented. In particular, the optics can also be adjusted for an ablation orthogonal to the bone or to a surface thereof.

In addition to the intervention tool, the endodevice can also be equipped with one or more further tools or instruments such as a gripper, a camera, a suction module or the like. Such further tools can be coupled to or directed by the moving formation such that they can benefit from the advantageous operability provided by the moving and fixing formations of the positioning unit.

Preferably, the laser arrangement comprises an optical fiber connectable to a laser source, the optical fiber has a distal end from which the laser beam is ejectable, and the laser beam propagating structure of the laser arrangement comprises the distal end of the optical fiber of the laser arrangement. Such embodiment of the laser arrangement allows for efficiently implementing the intervention tool propagating a laser beam at comparably little required space.

The laser arrangement can comprise further components which end or are located in or near the positioning unit. For example, the laser arrangement can have a suction device for removing debris of the tissue when being ablated by the laser, a camera for observing the laser ablation, a depth measuring device for identifying how deep the ablation goes into the tissue, an optical coherence tomography device for providing an overview of the ablation process, similar auxiliary devices or combinations thereof.

Preferably, the anchoring formation of the positioning unit comprises a leg with a foot portion fixable to the fixing tissue. The foot can be equipped with a fixing structure such as a pin or a suction mechanism. Such arrangement can allow for an efficient fixing and locating of the positioning unit.

Thereby, the moving formation of the positioning unit preferably has a first rail, a first slide and a first arm, wherein the first slide is mounted to the first rail such that it is movable along the first rail and the first arm is at one end region rotatably mounted to the first slide and at an opposite other end region rotatably mounted to the leg. Such a positioning unit allows for precise movements in three degrees of freedom. For example, like this an axial movement, a lateral movement and a pivoting, e.g. in the same plane, may be achieved. Such three degrees of freedom may be appropriate for many applications and intervention tools such as laser systems. Additionally, such a positioning unit allows for retracting the leg such that the positioning unit can be comparably compact when being introduced into the body.

The one or more legs can be configured to be flexibly adapted in length. Like this, a tilting movement can be implemented allowing for one or more additional degrees of freedom. Thereby, the legs can also comprise a pivoting or joint structure allowing an efficient tilting motion when being fixed to the fixing tissue. Alternatively or additionally, a pivoting or joint structure can be provided in the positioning unit, e.g. in a slide mounted to a rail, configured to rotate the positioning unit relative to the fixing tissue such that an additional degree of freedom of motion is provided. In such embodiments the leg(s) and/or pivoting/joint structure can be comprised by the fixing formation as well as the moving formation.

The moving formation of the positioning unit preferably has a second rail, a second slide and a second arm, wherein the second slide is mounted to the second rail such that it is movable along the second rail and the second arm is at one end region rotatably mounted to the second slide and at an opposite other end region rotatably mounted to the leg. Like this, guidance and movement of the leg can be implemented more stable and precise. Thereby, the first rail of the moving formation of the positioning unit and the second rail of the moving formation of the positioning unit preferably are parallel to each other.

Preferably, the anchoring formation of the positioning unit comprises a further leg with a foot portion fixable to the fixing tissue. Such a two or more leg implementation allows to provide an increased solidity of the positioning unit when it is fixed to the fixing tissue. Also such plural leg anchoring formation allows the positioning unit to walk along the fixing tissue. This can be achieved by alternatingly fixing one of the legs and moving the other one forward. Like this, the extent of the movement during intervention can be increased.

Thereby, the moving formation of the positioning unit preferably has a further first rail, a further first slide and a further first arm, wherein the further first slide is mounted to the further first rail such that it is movable along the further first rail and the further first arm is at one end region rotatably mounted to the further first slide and at an opposite other end region rotatably mounted to the further leg. Further, the moving formation of the positioning unit preferably has a further second rail, a further second slide and a further second arm, wherein the further second slide is mounted to the further second rail such that it is movable along the further second rail and the further second arm is at one end region rotatably mounted to the further second slide and at an opposite other end region rotatably mounted to the further leg. The further first rail of the moving formation of the positioning unit and the further second rail of the moving formation of the positioning unit preferably are parallel to each other.

Preferably, the foot is positioned at one lateral end of the positioning unit and the further foot is positioned at an opposite other lateral end of the positioning unit. Such lateral arrangement of the foot and the further food may allow providing advantageous stability.

For navigating the moving formation, the medical endodevice can be equipped with any suitable means such as a pneumatic or hydraulic formation, a shape memory alloy, an embedded motor, a microelectromechanical system (MEMS), or a combination thereof or the like. However, in a preferred embodiment, the liaising structure comprises at least one navigation wire fixed to the moving formation of the positioning unit. The term "wire" in this context can relate to any cable, rope, filament, fiber, yarn, cord, string, Bowden cable, torsion spring or the like of any suitable material. A suitable material could be biocompatible and should be robust enough for allowing controlling the positioning unit via the at least on wire. Such a wire allows for manipulating the positioning unit and in particular to activate the anchoring formation once the positioning unit is at an appropriate location as well as to operate the moving formation for adjusting the location of the intervention tool.

Thereby, the at least one navigation wire of the liaising structure preferably is mounted to the first slide of the moving formation of the positioning unit. Like this, the first slide can be moved along the first rail by manipulating such as pulling and pushing the wire. Analogously, further wires of the liaising structure can be mounted to the second slide, the further first slide and the further second slide. Also, the slides can be connected to springs which push or pull the slides away from the wires. Like this, the slides can be manipulated by pulling and releasing the wires. Also, rotational springs actuating spindles in the first or other slides can be provided for moving or advancing the slides.

Preferably, the positioning unit comprises a motor driving the first slide of the moving formation of the positioning unit. Like this, the first slide can be precisely moved along the first rail by the motor. Analogously, further motors can be comprised for the second slide, the further first slide and the further second slide. Thereby, the liaising structure comprises a communication wire connected to the motor. Like this, in operation, the motor can provide information outside the body and from there the motor can be controlled.

Preferably, the endodevice comprises a decoupling structure arranged or configured to decouple the positioning unit once it is fixed to the fixing tissue. In particular, the positioning unit can be decoupled from any guiding structure such as the tube of an endoscope, a rod or the like, and particularly from the liaising structure or a portion thereof. Thereby, the decoupling structure can be configured to decouple the positioning unit from remote or when the positioning unit is not directly accessible such as when it is positioned inside a body cavity or the like. In this context, the term "decouple" is not limited to physically separating the positioning unit. Rather, it can relate to detach or uncouple the positioning unit such that it is essentially independent from movements of the component it is decoupled from. Thus, by decoupling the positioning unit, it can be arranged essentially independent from movements of the element it is decoupled from, e.g. the guiding structure. For example, if the positioning unit is coupled to a tube or rod of an endoscope such decoupling allows for making the positioning unit independent from movements of the rod once the positioning unit is fixed. The decoupling structure can, e.g., be embodied by a soft or flexible part. Or, in case of a flexible endoscope, decoupling can be achieved by releasing the tension of the wires or Bowden cables controlling the endoscope such that the endoscope can no longer move the positioning unit.

Preferably, the decoupling structure is arranged or configured to recouple the positioning unit after being decoupled. Such a recoupling allows for reconnecting the positioning unit after intervention, e.g. cutting or drilling the target tissue, such that the endodevice together with the positioning unit can conveniently be removed from the body after intervention. To conveniently recouple the positioning unit the decoupling structure can be configured not to completely separate the liaising structure from the positioning unit but to keep a loose or flexible connection between the two.

Preferably, the positioning unit comprises a sensor arranged or configured to localize the positioning unit. Such sensors allow for preventing imaging such as computer tomography to be mandatory. Also, they allow for setting up a closed loop system automatically correcting any erroneous position changes of the positioning unit, e.g., induced by the body or by manipulation of the portions of the medical endodevice outside the body. Thereby, the sensor preferably is an optical sensor or any other suitable sensor such as an accelerometer, a gyroscope or any combination thereof. Such sensors can be sufficiently precise and fast.

Preferably, the endodevice comprises a robot arrangement connected to the intervention tool and the positioning unit via the liaising structure. Such a robot allows for a (semi-) automated controlling of the intervention tool and the positioning unit.

Preferably, the moving formation of the positioning unit is arranged or configured to dislocate the intervention tool relative to the target tissue in three to five or six degrees of freedom. Such arrangement might allow for sufficient, precise and fast positioning of the intervention tool. In other embodiments, the moving formation can also be arranged or configured to dislocate the intervention tool in more degrees of freedom. For example, movements can comprise lateral movements, back and forth movements, tilting movements, rotations about the longitudinal axis of the endodevice or the like. Such dislocation in any suitable number of degrees of freedom can be implemented by the moving formation described above. In particularly, the moving formation can be embodied with slides coupled to rails. Additionally or alternatively, the legs of the fixing formation can be length adjustable. Further, additionally or alternatively, one or more joint or pivoting structure can be implemented allowing a rotation or tilting movement. Thus, the moving formation can be equipped with any suitable element to achieve the desired degrees of freedom of motion. The moving formation can be embodied as or comprise a robot or robot like structure. For example, it can comprise a parallel robot or a similar device.

Preferably, the liaising structure of the endodevice comprises a tube ending at its distal end. The tube can be embodied to receive intervention tools or other instruments in operation. For example, in operation of the endodevice a drilling tool can be forwarded through the tube. Furthermore, the tube can end in the positioning unit such that variable tools or instruments can be precisely positioned by the positioning unit.

BRIEF DESCRIPTION OF THE DRAWINGS

The medical endodevice according to the invention are described in more detail hereinbelow by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
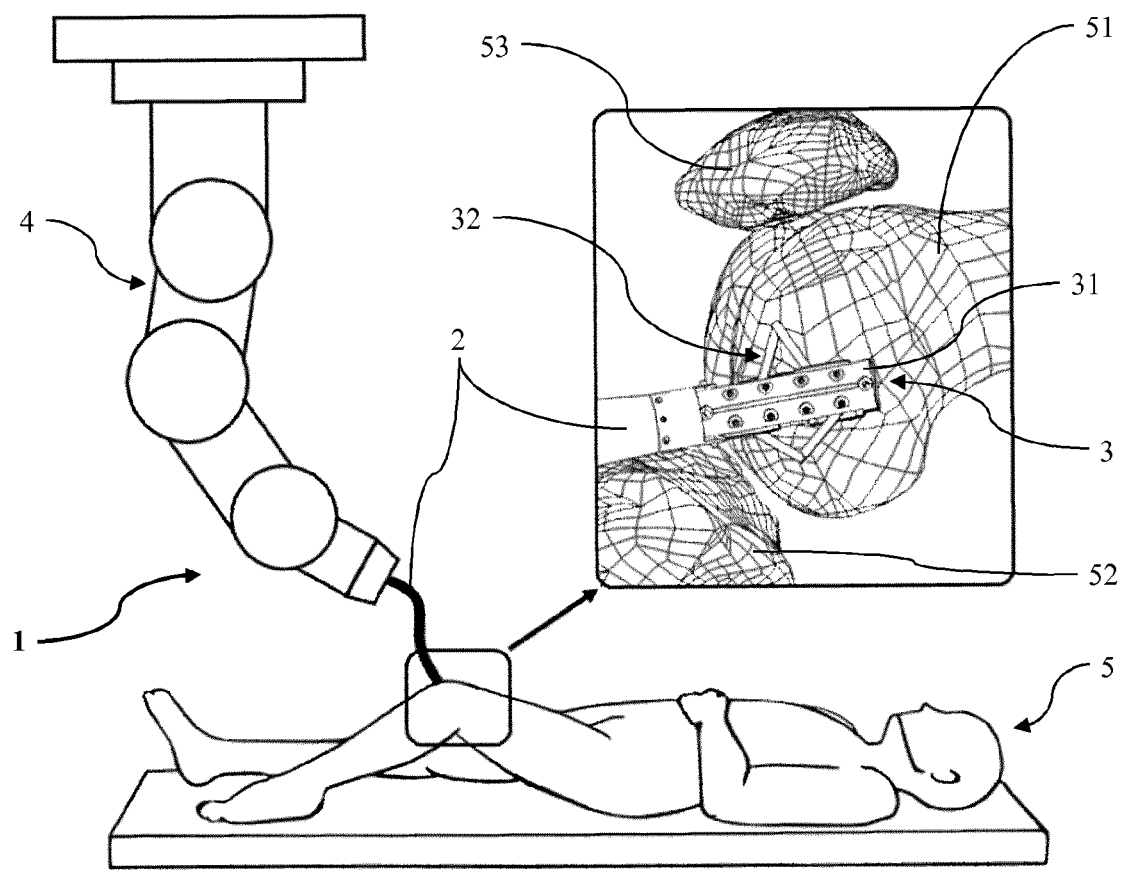
FIG. 1 shows an overview of an embodiment of a medical endodevice according to the invention in use, wherein a section comprising a positioning unit is additionally shown in an enlarged presentation.

FIG. 1 shows an overview of a first embodiment of an endodevice 1 according to the invention in operation. The endodevice 1 comprises an endoscope 2 as liaising structure equipped with a positioning unit 3 at its distal end and an arm robot 4 guiding and controlling the endoscope 2.

The endodevice 1 is used for an intervention in a knee of a patient 5. The endodevice 1 comprises an arm robot 4 and an endoscope 2 with a positioning unit 3. The endoscope 2 extends into the interior space of the knee as body cavity via an opening cut near a femur 51, a tibia 52 and a patella 53 of the patient 5.

The positioning unit 3 has a base body 31 fixed to a lower extremity of the femur 51 as fixing tissue. As described in more detail below, the positioning unit 3 is equipped with a moving formation 32 for moving the base body 31 along the femur 51. The base body 31 houses adjustable mirrors as intervention tool in form of a laser beam propagating structure of a laser arrangement of the endodevice 1. The adjustable mirrors are arranged to direct a pulsed laser beam suitable to ablate and cut the lower extremity of the femur 51 as target tissue (not visible in FIG. 1). The laser beam pulses are guided towards the positioning unit 3 and the adjustable mirrors via an optical fibre of the endoscope 2.

Figure 2:
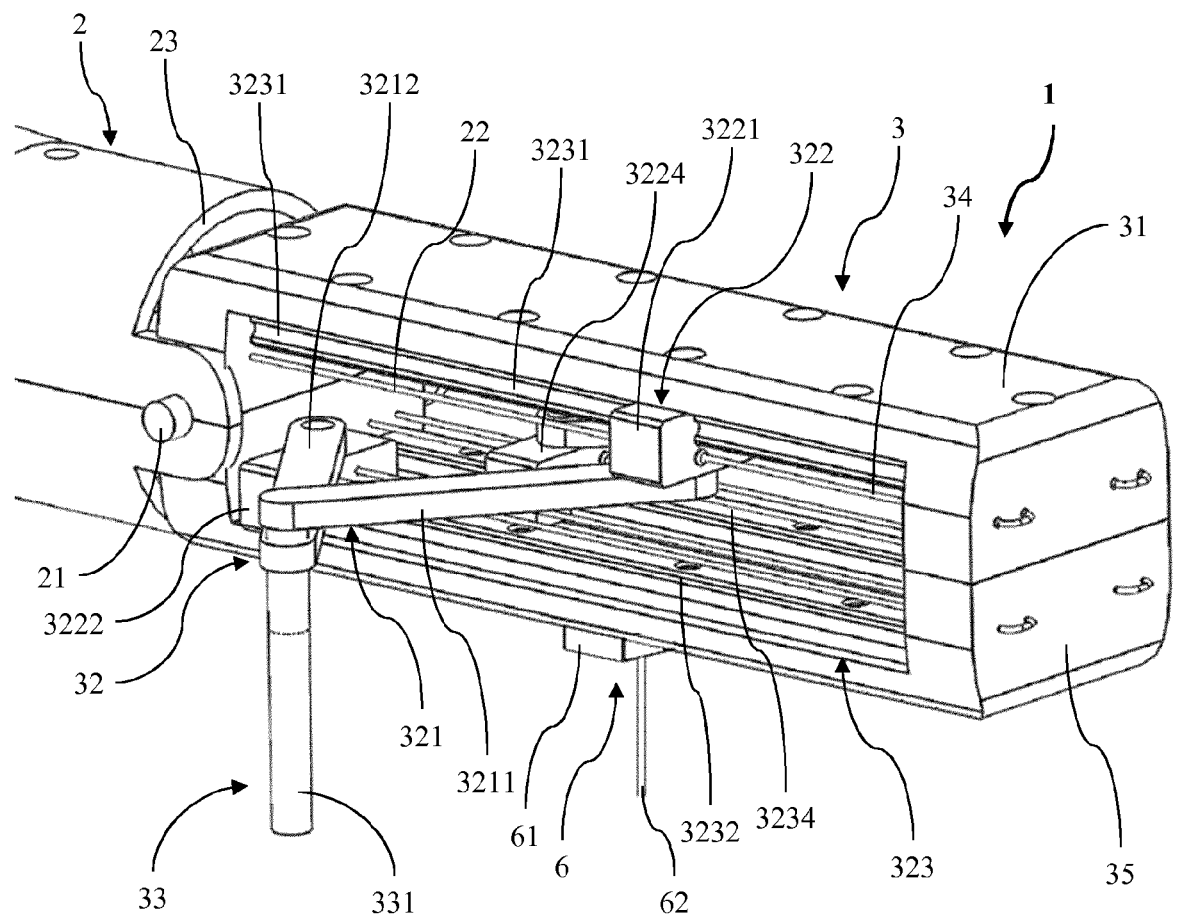
FIG. 2 shows a first perspective view of the positioning unit of the endodevice of FIG. 1.

In FIG. 2 the positioning unit 3 mounted to the distal end 23 of the endoscope 2 via a joint 21 is shown in more detail. It comprises the base body 31, the moving formation 32 and an anchoring formation 33. The anchoring formation 33 comprises a post-like straight vertical leg 331 which at its bottom end, i.e. its foot portion, is provided with a tip. The tip can be attached to the lower extremity of the femur 51 as fixing tissue. Like this, the positioning unit 3 can be fixed to the femur 51 close to the location of its lower extremity to be cut by the laser beam.

The moving formation 32 has straight horizontal arms 321, slides 322 and rails 323. The arms 321 comprise a first arm 3211 and a second arm 3212 which at a first longitudinal end are rotatably mounted to a top end of the leg 331 of the anchoring formation 33. Thereby, the first and second arms 3211, 3212 can be pivoted about a longitudinal axis of the leg 331.

The slides 322 comprise a first slide 3221 mounted on a first rail 3231 of the rails 323 and a second slide 3222 mounted on a second rail 3232 of the rails 323. The first and second rails 3231, 3232 extend along the base body 31 from the endoscope 2 to a longitudinal end 35 of the positioning unit 3. The first rail 3231 is positioned on top of and parallel to the second rail 3232.

A second longitudinal end of the first arm 3211 is rotatably mounted to the first slide 3221 and a second longitudinal end of the second arm 3212 is rotatably mounted to the second slide 3222. By moving the first and second slides 3221, 3222 the first and second arms 3211, 3212 are pivoted about the leg 331 which is fixed to the femur 51. Thereby, as described in more detail below, the position of the base body 31 together with the intervention tool can be adjusted.

For moving the slides 322 along the rails 323 they are connected to navigation or guiding wires 22 of the endoscope 2. Each of the wires 22 is at one end attached to one of the slides 322 and at its other end connected to the arm robot 4 for control. Furthermore, between each of the slides 322 and the longitudinal end 35 of the positioning unit 3 an elastic cable 34 as spring is arranged pulling the respective slide 322 towards the longitudinal end 35. In order to move one of the slides 322 towards the distal end 23 of the endoscope 2 it is pulled by the respective wire 22. If no or a reduced force acts on the wire 22, the respective slide 322 is moved towards the longitudinal end 35 by the respective elastic cable 34.

At a lower side of the positioning unit 3 a laser propagator 6 is mounted as an intervention tool. The laser propagator 6 comprises a beam redirection element 61 such as a mirror, a lens, a combination thereof or the like which directs a laser beam 62 towards the femur 51. The beam redirection element 61 can be dislocated by the movement formation 32 relative to the femur 51. In addition thereto, the beam redirection element 61 can be moved relative to the positioning unit 3 in order to precisely direct beam 62 to and along the femur 51. For example, particularly in embodiments where the beam redirection element is or has a mirror, the mirror can be tilted or turned relative to the positioning unit 3.

Figure 3:
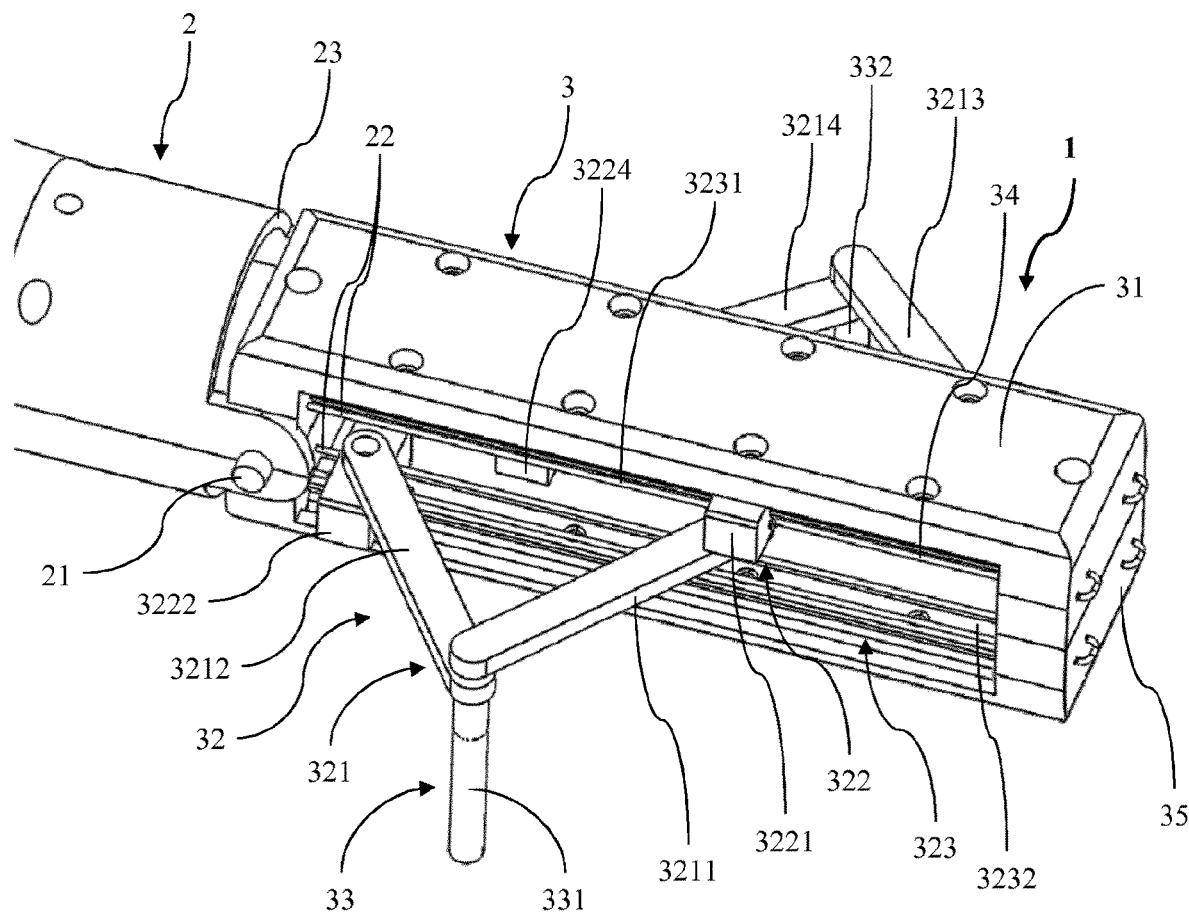
FIG. 3 shows a second perspective view of the positioning unit of the endodevice of FIG. 1.
Figure 4:
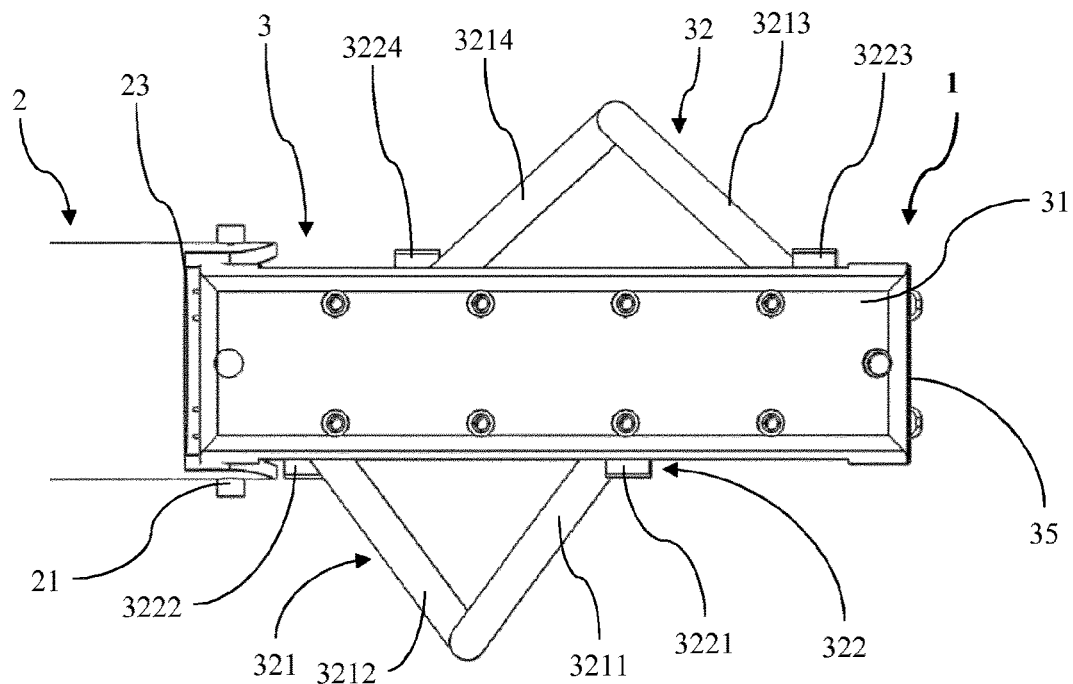
FIG. 4 shows a top view of the positioning unit of the endodevice of FIG. 1.

As can be seen in FIG. 3 and FIG. 4, the moving formation 32 and the anchoring formation 33 are mirror-symmetrically formed. In particular, they comprise a further first arm 3213, a further second arm 3214, a further first slide 3223, a further second slide 3224, a further first rail (not visible in the FIGS.), a further second slide 3234 and a further leg 332. Similar as described above, the further first and second arms 3213, 3214 are at one end rotatably mounted to the further leg 332 and at the other end rotatably mounted to the further first and second slides 3223, 3224. The further first and second slides 3223, 3224 are slidably mounted to the further first and second slides 3234, respectively.

Figure 5:
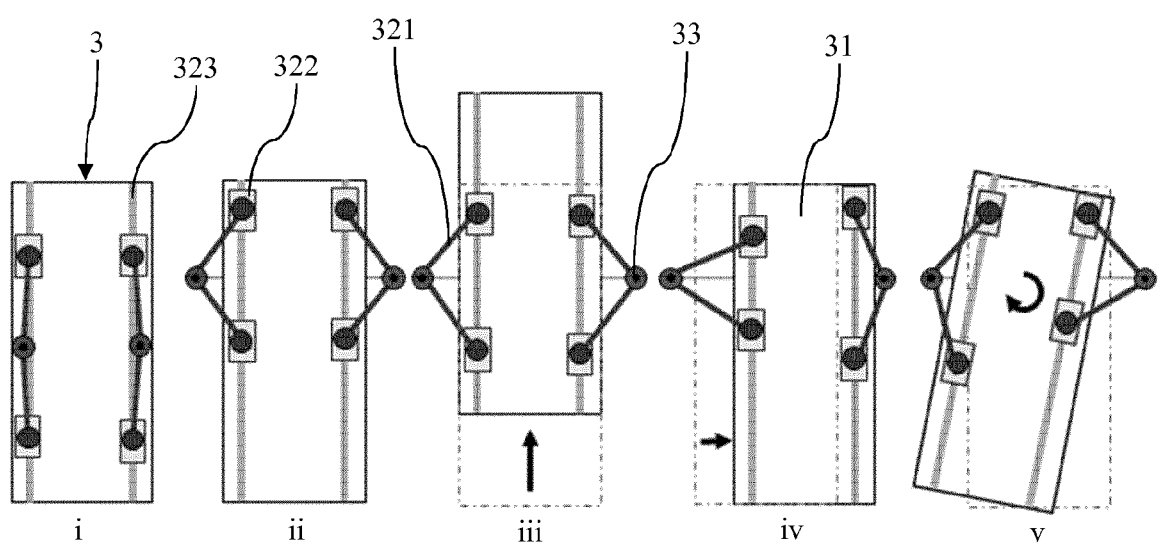
FIG. 5 shows top views illustrating movements of the positioning unit of the endodevice of FIG. 1.

FIG. 5 shows the positioning unit 3 of the endodevice 1 in five different positions i to v in order to illustrate the operation of the moving formation 32 and the fixing formation 33. In position i, in FIG. 5 this is the left most position, the slides 322 are at a maximum distance to each other such that the arms 321 are stretched. In particular, the first and second slides 3221, 3222 are moved along the respective rails 3231, 3232 apart from each other, such that the first and second arms 3211, 3222 are pivoted about the leg 331 to be at almost 180° to each other. Analogously, the further first and second slides 3223, 3224 are moved along the respective further first and second rails 3234 apart from each other, such that the further first and second arms 3213, 3214 are pivoted about the further leg 332 to be at almost 180° to each other. In position i, the leg 331 and the further leg 332 are retracted towards the base body 31. Like this, the positioning unit 3 is folded such that it requires comparably little space and that it can conveniently be forwarded into the body of the patient 5 by means of the endoscope 2.

In position ii, in FIG. 5 this is the second left position, the positioning unit 3 is at a target location. There, the distance between each pair of the slides 322 is reduced such that an angle between the respective arms is reduced. Thereby, the legs 33 are laterally moved in an outward direction. There, they are fixed to the target tissue, i.e. the lower extremity of the femur 51. The positioning unit 3 is decoupled from the endoscope such that it is independently fixed to the femur 51.

In position iii, in FIG. 5 this is the middle position, the base body 31 is axially or straightly moved in a forward direction. This is achieved by simultaneously moving the slides 322 along the rails 323. The legs 33 are still fixed to the femur 51.

In position iv, in FIG. 5 this is the second right position, the positioning unit 3 is laterally moved to the right. For that, the angle between the first arm 3211 and the second arm 3212 is increased by moving the first and second slides 3221, 3222 towards each other as well as, simultaneously, the angle between the further first arm 3213 and the further second arm 3214 is decreased by moving the further first and second slides 3223, 3224 apart from each other.

In position v, in FIG. 5 this is the right most position, the positioning unit 3 is pivoted clock-wise by appropriately adjusting the angle between the first and second arms 3111, 3112 in coordination with the angle between the further first and second arms 3113, 3114.

As can be seen in FIG. 5, the moving formation 32 allows the positioning unit 3 to be moved in three degrees of freedom, i.e. a forward-backward or axial movement, a left-right or lateral movement and a pivoting movement. This allows for precisely positioning the intervention tool in

The invention claimed is:

1. A medical endodevice for an intervention inside a human or animal body, comprising:
   an elongated liaising structure having a distal end arrangeable inside a body of a human or animal being and a proximal end arrangeable outside the body while the distal end is inside the body,
   a positioning unit mounted at the distal end of the liaising structure, and
   an intervention tool arranged to manipulate a target tissue inside the human or animal body, wherein the intervention tool is arranged at the positioning unit at the distal end of the liaising structure, and
   wherein the positioning unit has a moving formation arranged to dislocate the intervention tool relative to the target tissue, the moving formation being configured to allow the positioning unit to perform defined movement in three to five degrees of freedom, and
   wherein the positioning unit has an anchoring formation arranged to fix the moving formation to a fixing tissue inside the human or animal body such that the target tissue is positioned in a workspace of the intervention tool, and
   a decoupling structure arranged to decouple the positioning unit once it is fixed to the fixing tissue.

2. The medical endodevice of claim 1, comprising a laser arrangement, wherein the intervention tool is a laser beam propagating structure of the laser arrangement.

3. The medical endodevice of claim 2, wherein the laser beam propagating structure of the laser arrangement comprises an adjustable optics arranged to direct the laser beam in various directions.

4. The medical endodevice of claim 2, wherein
   the laser arrangement comprises an optical fiber connectable to a laser source,
   the optical fiber has a distal end from which the laser beam is ejectable, and
   the laser beam propagating structure of the laser arrangement comprises the distal end of the optical fiber of the laser arrangement.

5. The medical endodevice of claim 1, wherein the anchoring formation of the positioning unit comprises a leg with a foot portion fixable to the fixing tissue.

6. The medical endodevice of claim 5, wherein the moving formation of the positioning unit has a first rail, a first slide and a first arm, wherein the first slide is mounted to the first rail such that it is movable along the first rail, and the first arm is at one end region rotatably mounted to the first slide and at an opposite other end region rotatably mounted to the leg.

7. The medical endodevice of claim 6, wherein the anchoring formation of the positioning unit comprises a further leg with a foot portion fixable to the fixing tissue.

8. The medical endodevice of claim 7, wherein the moving formation of the positioning unit has a further first rail, a further first slide and a further first arm, wherein the further first slide is mounted to the further first rail such that it is movable along the further first rail, and the further first arm is at one end region rotatably mounted to the further first slide and at an opposite other end region rotatably mounted to the further leg.

9. The medical endodevice of claim 6, wherein the liaising structure comprises at least one navigation wire connected to the moving formation of the positioning unit.

10. The medical endodevice of claim 9, wherein the at least one navigation wire of the liaising structure is mounted to the first slide of the moving formation of the positioning unit.

11. The medical endodevice of claim 1, wherein the positioning unit comprises a sensor arranged to localize the positioning unit.

12. The medical endodevice of claim 11, wherein the sensor is an optical sensor.

13. The medical endodevice of claim 1, comprising a robot arrangement connected to the intervention tool and the positioning unit via the liaising structure.

14. The medical endodevice of claim 1, wherein the decoupling structure is arranged to recouple the positioning unit after being decoupled.

* * * * *